United States Patent
Albarella et al.

(10) Patent No.: US 7,767,822 B2
(45) Date of Patent: Aug. 3, 2010

(54) WATER-SOLUBLE TETRAZOLIUM SALTS

(75) Inventors: James P. Albarella, Granger, IN (US);
Steven W. Felman, Granger, IN (US);
John J. Landi, Elkhart, IN (US); Karen L. Marfurt, Edwardsburg, MI (US)

(73) Assignee: Bayer Healthcare LLC, Tarrytown, NY (US)

( * ) Notice: Subject to any disclaimer, the term of this patent is extended or adjusted under 35 U.S.C. 154(b) by 196 days.

(21) Appl. No.: 11/794,782

(22) PCT Filed: Jan. 13, 2006

(86) PCT No.: PCT/US2006/001307
§ 371 (c)(1),
(2), (4) Date: Jul. 5, 2007

(87) PCT Pub. No.: WO2006/076619
PCT Pub. Date: Jul. 20, 2006

(65) Prior Publication Data
US 2008/0125471 A1 May 29, 2008

Related U.S. Application Data

(60) Provisional application No. 60/643,893, filed on Jan. 14, 2005.

(51) Int. Cl.
*C07D 277/20* (2006.01)
*C07D 257/04* (2006.01)
(52) U.S. Cl. ............... 548/146; 548/190; 548/250
(58) Field of Classification Search ............ 548/146, 548/190, 250
See application file for complete search history.

(56) References Cited

U.S. PATENT DOCUMENTS

| | | | | |
|---|---|---|---|---|
| 2,073,600 | A | 3/1937 | Bayer et al. | 260/44 |
| 5,126,275 | A | 6/1992 | Hatch et al. | 436/169 |
| 5,185,450 | A | 2/1993 | Owen | 548/194 |
| 5,196,314 | A | 3/1993 | Town et al. | 435/25 |
| 5,250,695 | A | 10/1993 | Blatt et al. | 548/150 |
| 5,290,536 | A | 3/1994 | Köcher et al. | 424/7.1 |
| 5,300,637 | A | 4/1994 | Hatch et al. | 518/162 |
| 5,322,680 | A * | 6/1994 | Beck et al. | 436/73 |
| 5,360,595 | A | 11/1994 | Bell et al. | |
| 6,063,587 | A | 5/2000 | Ishiyama et al. | 435/7.4 |
| 6,183,878 | B1 | 2/2001 | Berneth et al. | 428/583 |
| 6,207,292 | B1 | 3/2001 | Berneth et al. | 428/583 |
| 6,277,307 | B1 | 8/2001 | Berneth et al. | 252/583 |
| 6,586,199 | B2 | 7/2003 | Ouyang et al. | 435/26 |
| 2004/0132004 | A1 | 7/2004 | Nakamura et al. | 435/4 |

FOREIGN PATENT DOCUMENTS

| | | |
|---|---|---|
| DE | 2 147 466 | 3/1973 |
| EP | 0 476 455 A2 | 6/1991 |
| EP | 0 476 457 A | 3/1992 |
| JP | 58113181 | 7/1983 |
| WO | WO 98/37157 | 8/1998 |

OTHER PUBLICATIONS

Dorwald F. A. (Side Reactions in Organic Synthesis, 2005, Wiley: VCH, Weinheim p. IX of Preface. 19 pages total).*
Written Opinion of the International Searching Authority corresponding to co-pending International Patent Application No. PCT/US2006/001307, European Patent Office, dated May 31, 2006, 6 pages.
International Search Report corresponding to co-pending International Patent Application No. PCT/US2006/001307, European Patent Office, dated May 31, 2006, 6 pages.
M. Ishiyama et al., "A Highly Water-Soluble Disulfonated Tetrazolium Salt as a Chromogenic Indicator for NADH as Well as Cell Viability," Talanta 44 (1997) 1299-1305, © 1997 Elsevier Science B.V.
C. V. Gheorghiu et al., "Benzothiazole Derivatives. Disubstituted Hydrazones and Thiosemicarbazides," Chemical Abstracts, American Chemical Society, vol. 53, col. 15653-19464, Sep. 10-Oct. 25, 1959, 2 pages.

* cited by examiner

*Primary Examiner*—Kamal A Saeed
*Assistant Examiner*—Samantha L Shterengarts
(74) *Attorney, Agent, or Firm*—Nixon Peabody LLP

(57) ABSTRACT

Thiazolyl tetrazolium salts with increased solubility in aqueous solutions have alkylammonium alkoxy substituents, preferably trimethyl ammonium propoxy groups substituents, on phenyl rings attached to the tetrazolium ring. Thiazolyl tetrazolium salts with increased solubility in aqueous solutions have alkyl ammonium alkoxy substituents, preferably trimethyl ammonium propoxy groups substituents, on phenyl rings attached to the tetrazolium ring, e.g. the compounds of the general formula shown below. Formula $(A-)_a$.

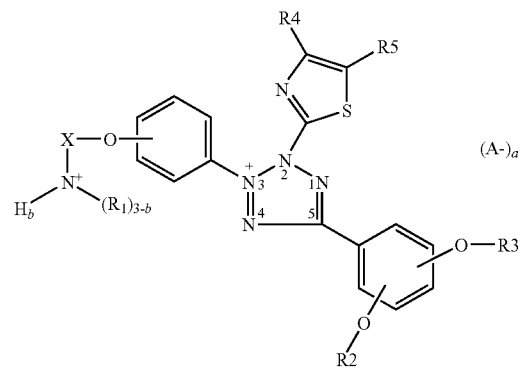

14 Claims, 7 Drawing Sheets

EX. 1

EX. 2

EX. 3

EX. 4

EX. 5

EX. 6

EX. 7

EX. 8

EX. 9

WATER-SOLUBLE TETRAZOLIUM SALTS

CROSS-REFERENCE TO RELATED APPLICATIONS

This application claims priority to Application No. 60/643,893 filed on Jan. 14, 2005, which is incorporated by reference in its entirety.

FIELD OF THE INVENTION

This invention is related to the analysis of biological samples for medical purposes.

BACKGROUND OF THE INVENTION

Analysis of biological samples often involves methods in which a color is developed that is proportional to the amount of an analyte in the sample. For example, enzymes may be employed to oxidize the analyte of interest and the extent of reaction is shown by a color change of an indicator compound. Of particular interest herein is the family of tetrazolium salts that is used as indicators. Such salts are reduced to formazan dyes by reducing substances. To measure an analyte, an enzyme (e.g., an NAD-dependent dehydrogenase enzyme), oxidizes the analyte to produce the reduced form (e.g., NADH), that reacts with a tetrazolium salt to produce a colored formazon. A mediator may be needed to facilitate the reaction. Since the amount of NADH produced by the analyte reaction is proportional to the amount of formazan produced, the amount of the analyte can be measured indirectly by the color formed.

Tetrazolium salts have been used in various applications. But, in particular, they have been used in the medical field for measuring the analytes in various biological fluids such as blood, urine, plasma, and serum. These indicators often are used with reagent systems placed on test strips which, when in contact with a fluid sample, react with the analyte of interest and display a color that indicates the amount of the analyte present. Although in some instances, the color change can be read visually by reference to color charts, more accurate readings may be made spectrophotometrically by instruments that are designed for that purpose. Typically, light is directed onto the test strip and the reflected light is measured to determine the effect of the color change on the strip.

Tetrazolium salts should produce formazans that absorb light at wave lengths that avoid interference by substances in the sample, such as the hemoglobin in whole blood. Consequently, a family of thiazolyl tetrazolium salts has been developed that produce formazans that absorb light having wavelengths above about 640 nm, such as those produced by LEDs used as light sources. LEDs provide a narrow range of wavelengths that vary only about ±5 nm. Such thiazolyl tetrazolium salts are disclosed in several U.S. patents such as U.S. Pat. Nos. 5,126,275; 5,322,680; 5,300,637; and 5,290,536.

Most biological samples are aqueous in nature, so it is desirable that the indicators be soluble in the sample. However, many of the tetrazolium salts are not very soluble. One supplier of tetrazolium salts, Dojindo Laboratories, has a line of indicators that have been made more soluble by the addition of sulfonic acid groups to the indicator molecule. See U.S. Pat. No. 6,063,587 and published Japanese patent applications JP58113181 A2 and JP58113182 A2. Their WST series of tetrazolium salt indicators are often mentioned in patents disclosing analytical methods. One example is found in U.S. Pat. No. 6,586,199. The solubility of the WST series of tetrazolium salts is reported to be about 10 mg/mL water. Solubility also may be increased when certain sulfonate and phosphonate counterions of tetrazolium salts are used such as disclosed in U.S. Pat. No. 5,250,695.

Other patents discussing tetrazolium salt indicators include EP0476455 B1; US 2004/0132004 A1; WO 98/37157; U.S. Pat. No. 6,183,878 B1; U.S. Pat. No. 6,207,292 B1; U.S. Pat. No. 6,277,307 B1; DE 21 47 466; U.S. Pat. No. 5,185,450; U.S. Pat. No. 5,196,314.

The present inventors wanted to improve the solubility of the thiazolyl tetrazolium salts while retaining their ability to provide a relatively flat spectral response from their formazans in the region of 600 to 640 nm in response to incident light provided by LEDs. As will be seen in the description of the invention below, they have succeeded in providing thiazolyl tetrazolium salts having greater solubility, while retaining the desired spectral response.

SUMMARY OF THE INVENTION

The invention includes novel thiazolyl tetrazolium salts. Some have been found to have better solubility in water than a related proprietary thiazolyl tetrazolium salt. Improving solubility makes them more easily applied to test strips used for measuring analytes in biological samples (e.g., glucose in blood samples). The tetrazolium salts are characterized by having an alkyl ammonium alkoxy substituent that increases solubility. According to one embodiment, the tetrazolium salts are defined in the following formula.

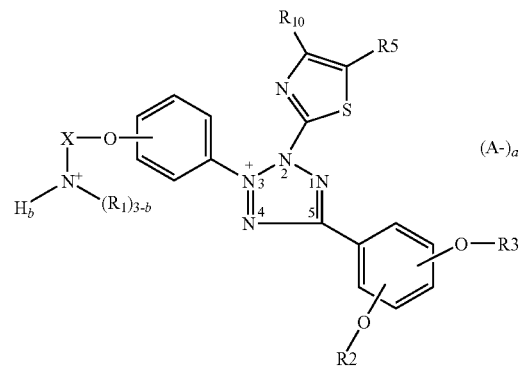

where:
A=counter-ion
X=1-6C alkyl or heteroalkyl
a=1-3
b=0-3
$R_1$=1-6C alkyl
one of $R_2$ and $R_3$ is allyl and the other is $XN+H_b(R_1)_{3-b}$ or $R_2$ and $R_3$ form a methylene dioxy group
one of $R_4$ or $R_5$ is halogen and the other is halogen substituted 1-6C alkyl, one or both of $R_4$ and $R_5$ are $XN+H_b(R_1)_{3-b}$, or
$R_4$ and $R_5$ are joined to form an aromatic or hetero aromatic ring or a substituted aromatic or a substituted hetero aromatic ring The formula diagramed above represents novel thiazolyl tetrazolium salts, that is they contain a thiazole ring attached to the tetrazolium ring at the 2 nitrogen position. Furthermore, they each have a phenyl ring attached at the 3 nitrogen position and another phenyl ring attached at the 5 position on the tetrazolium ring. Increased solubility relative to a proprietary thiazoyl tetrazolium salt designated HTC-045 herein is achieved by attaching one or more alkyl ammonium alkoxy groups to the thiazoyl tetrazolium salt. The alkyl ammonium alkoxy groups may be attached to the thiazolyl ring as $R_4$ and/or $R_5$, or substituted on an aromatic or hetero aromatic ring formed by $R_4$ and $R_5$. In preferred embodiments, the alkyl ammonium alkoxy groups are substituents on the phenyl rings attached to the tetrazolium ring. In more preferred embodiments, the alkyl ammonium alkoxy group is trialkyl ammonium propoxy. Benzothiazolyl tetrazolium salts are preferred compounds having increased solubility.

In another aspect of the invention, the thiazolyl tetrazolium salts are used as chromogenic indicators to detect the presence of reducing substances (e.g., NADH), in analysis of biological samples using enzymes to oxidize analytes, such as in the determination of the glucose content of blood.

DESCRIPTION OF THE PREFERRED EMBODIMENTS

Definitions

Figure 1:
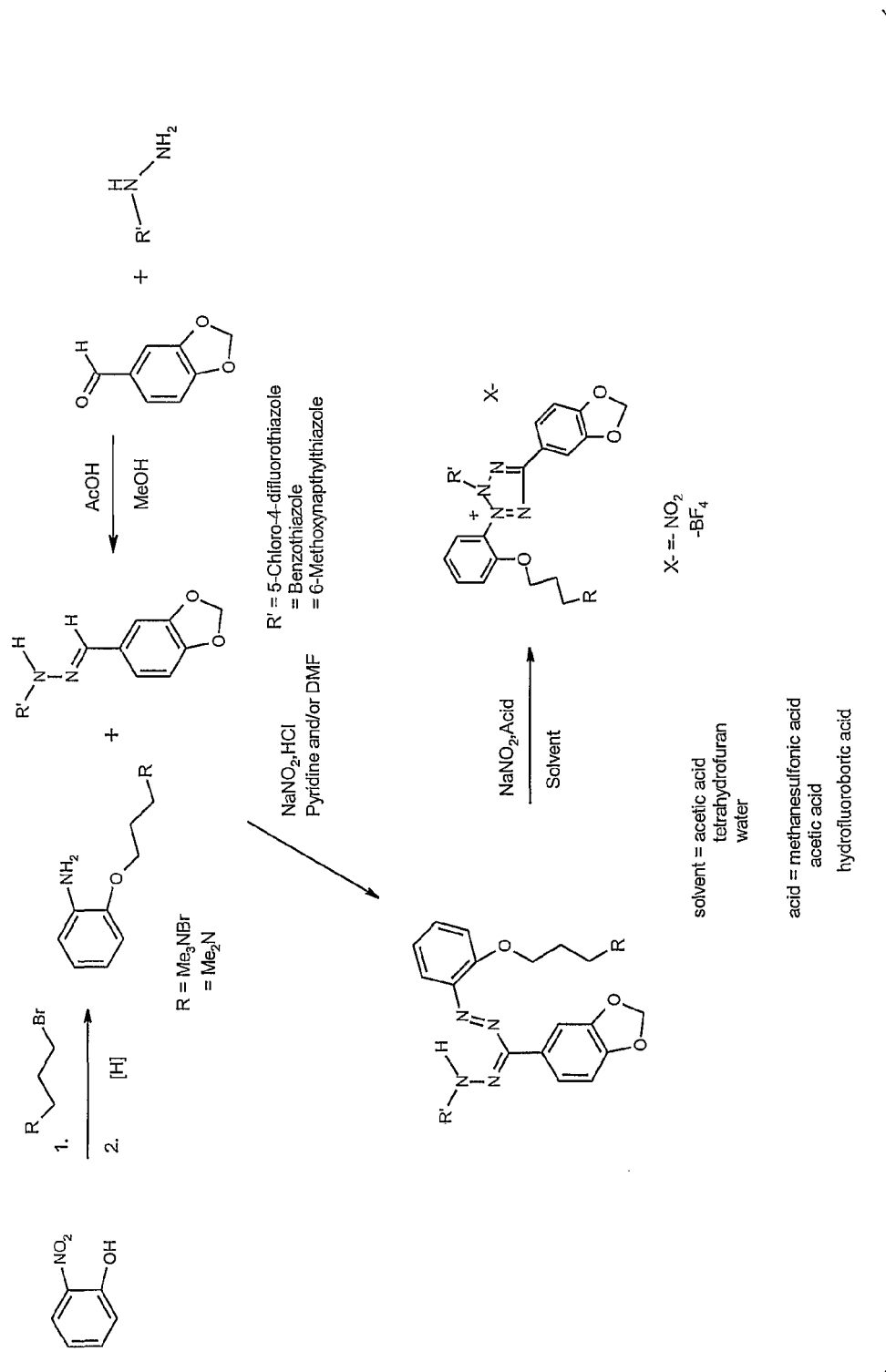
FIG. 1 is a diagram of a first method of preparing compounds of the examples.

The following definitions apply to the substituents of the thiazolyl tetrazolium salts of the invention.

"1-6C"—means a residue having 1 to 6 carbon atoms

"alkyl"—means linear and branched hydrocarbon residues of the general formula $C_nH_{2n+1}$ "heteroalkyl"—means linear and branched hydrocarbon residues containing hetero atoms attached to adjacent carbon atoms "alkoxy"—means the residue —OR where R is alkyl "methylene dioxy"—means the divalent residue of the formula —O—$CH_2$—O—

"halogen"—means fluorine, chlorine, iodine, and bromine

"halogen substituted 1-6C alkyl"—means a linear or branched residue having the general formula $C_nH_{2n-1}Y_2$ where Y is a halogen "aromatic ring"—means a benzene or napthalene ring "heteroaromatic ring"—means a pyridine or quinoline ring "counter-ion"—means an ion residue from reagents used in preparing the tetrazolium salts, (e.g., nitrite, phosphate, hydrogenphosphate, dihydrogenphosphate, hydrogen sulfate, sulfate, hydrogen carbonate, carbonate, methane sulfonate, fluoroborate, bromide, chloride, iodide, or combinations thereof)

"test salt"—is an abbreviation of tetrazolium salt

Thiazolyl Tetrazolium Salts

As disclosed in U.S. Pat. No. 5,126,275, formazans from thiazolyl tetrazolium salts are characterized by having a reflectance spectrum exhibiting an extended plateau above about 600-650 nm, which is useful in equipment using LEDs as a light source. A sample is brought into contact with a reaction system that produces a color indicating the amount of an analyte present in the sample. The light returned from the test area is detected and correlated with the analyte content. In one important example, glucose dehydrogenase in the presence of $NAD^+$ catalyzes the oxidation of glucose in blood samples. The reduced NADH is reoxidized by a enzyme mediator, such as diaphorase, which catalyzes the reduction of the tetrazolium salt to a formazan. The color change produced is proportional to the amount of NADH produced from the oxidization of glucose and indirectly proportional to the amount of glucose present in the sample. The color change from the conversion of thiazolyl tetrazolium salts to the colored formazan can be measured by exposing it to a light source. Light returned from the colored test area is detected and converted by a suitable algorithm into the amount of analyte in the sample. Although described here with respect to NAD-NADH, the tetrazolium salts of the invention have broader applications, including their use with dehydrogenase enzymes having other co-factors, such as PQQ and FAD.

Since the thiazolyl tetrazolium salts and their corresponding formazans should be soluble in the reaction mixture applied to test strips used to detect analytes, it was an object of the inventors to improve the solubility of thiazole tetrazolium salts, while maintaining their ability to provide formazans that have a relatively flat reflectance spectrum in the 600-640 nm range. The inventors have found a family of novel thiazolyl tetrazolium salts that include compounds which meet their objectives. These salts are represented by the following general formula:

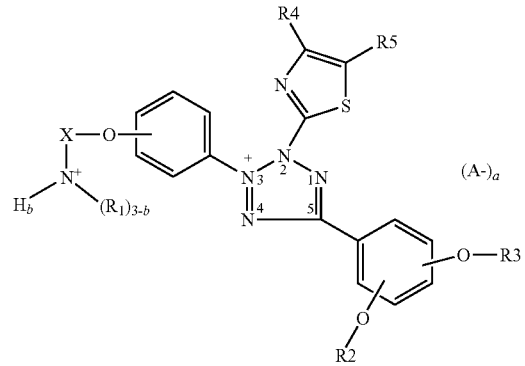

where:

A=counter-ion

X=1-6C alkyl or heteroalkyl a=1-3 b=0-3

$R_1$=1-6C alkyl one of $R_2$ and $R_3$ is alkyl and the other is $XN+H_b(R_1)_{3-b}$ or $R_2$ and $R_3$ form a methylene dioxy group one of $R_4$ or $R_5$ is halogen and the other is halogen substituted 1-6C alkyl, one or both of $R_4$ and $R_5$ are $XN+H_b(R_1)_{3-b}$, or $R_4$ and $R_5$ are joined to form an aromatic or hetero aromatic ring or a substituted aromatic or substituted hetero aromatic ring The tetrazolium salts of the invention also may be separated into substituted thiazoyl tetrazolium salts and substituted benzothiazolyl tetrazolium salts, as shown in the following formulas of particular interest.

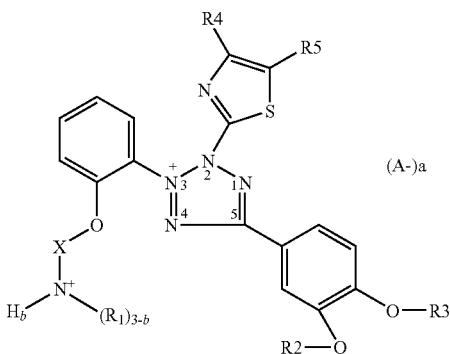

where:
A=counter-ion
X=1-6C alkyl
a=1-3
b=0-3
R$_1$=1-3C alkyl
one of R$_2$ and R$_3$ is 1-4C alkyl and the other is XN+H$_b$(R$_1$)$_{3-b}$ or R$_2$ and R$_3$ are joined as a methylene dioxy group
R$_4$=CHF$_2$
R$_5$=halogen

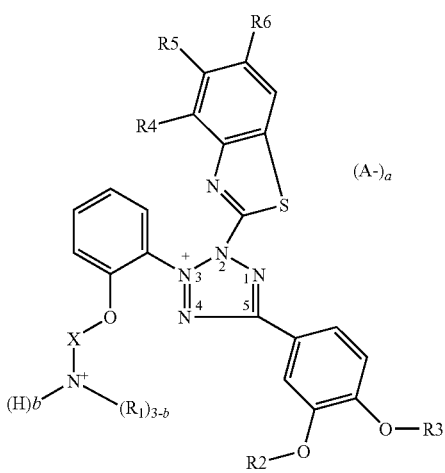

A=counter-ion
X=1-6C alkyl
a=1-3
b=0-3
R$_1$=1-3C alkyl
one of R$_2$ and R$_3$ is 1-4C alkyl and the other is XN+H$_b$(R$_1$)$_{3-b}$, or R$_2$ and R$_3$ are joined as a methylene dioxy group
R$_4$ and R$_5$ are H, or R4 and R5 are joined to form an aromatic ring
R$_6$=1-4C alkoxy, hydrogen, or halogen The solubility of these compounds (I and II) will be shown in the examples below. Improving solubility of the thiazolyl tetrazolium salts should reduce the time required to obtain test results and provide better linearity at high analyte levels. Also, improved water solubility should facilitate formulating a one-reagent mixture, which will be easier and less expensive to manufacture.

Methods of Making Tetrazolium Salts of the Invention

Figure 2:
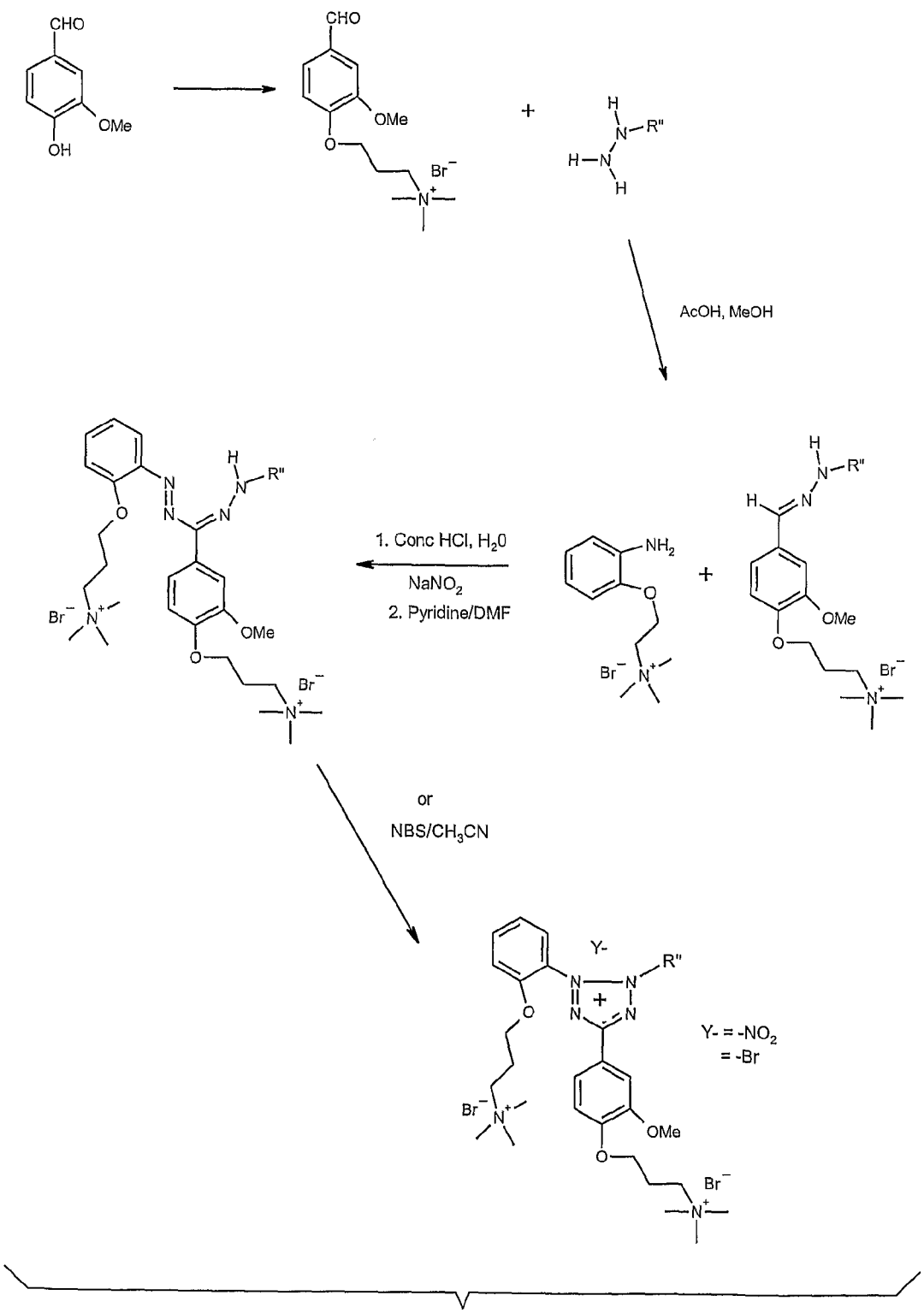
FIG. 2 is a diagram of a second method of preparing compounds of the examples.

In U.S. Pat. No. 5,126,275, methods of making thiazolyl tetrazolium salts are described. The methods involve the reaction of a hydrazone with diazotized aniline to produce a formazan, which is then oxidized to the tetrazolium salt. New methods to be described for making the compounds of the invention were developed to introduce one (Scheme 1) or two (Scheme 2) polar groups into the preferred tetrazolium salts of compounds I and II. FIGS. 1 and 2 illustrate these two methods. The following examples further illustrate this invention.

Scheme 1 is used to produce tetrazolium salts in which the phenyl substituent at the 5 position on the tetrazolium ring has a methylene dioxy substituent. In Scheme 1, a trimethyl ammonium propoxy group is substituted on the phenyl substituent at the 3 position on the tetrazolium ring. In Scheme 1, O-nitrophenol is reacted with 3-bromopropyl trimethyl ammonium bromide to form 3-(2-nitrophenoxy) propyltrimethyl ammonium bromide and then hydrogenated to the equivalent aniline. Reaction of that compound with a hydrazone containing a substituted thiazolyl ring and a phenyl ring with a methylene dioxy substituent yields the formazan. The formazan is then oxidized to the tetrazolium salt. The hydrazone is formed from the reaction of a substituted benzaldehyde with a substituted hydrazine containing the desired substituents for the tetrazolium salt.

Scheme 2 is used to produce tetrazolium salts in which the phenyl substituent at the 5 position on the tetrazolium ring has a trimethyl ammonium propoxy groups substituted at either (or both) the 3 or 4 position. As in Scheme 1, a trimethyl ammonium propoxy group is substituted on the phenyl substituent at the 3 position on the tetrazolium ring. In Scheme 2, 4-Hydroxy-3 methoxy benzaldehyde is reacted with 3-bromopropyltrimethylammonium bromide to add a trimethylammonium propoxy group to the benzaldehyde. The product is reacted with a substituted hydrazine to produce a hydrazone. The hydrazone is reacted with the 3-(2-amino phenoxy) propyl trimethyl ammonium bromide produced in the first step of Scheme 1 to produce the formazan, which is converted to the tetrazolium salt.

It will be seen in the results below that the solubility appears to be affected by the counterions associated with the tetrazolium salts. The counterions result from reagents used in the process and can be varied to provide preferred counterions. Alternatively, counterions may be replaced, for example by ion-exchange methods.

In the following non-limiting examples, the products of each step were identified by spectrophotometric methods and the results presented for each product.

EXAMPLE 1

Preparation of 5-Benzo[1,3 dioxol-5-yl]-3-[2-(3-trimethylammonium) propoxy-phenyl]-2-(5-chloro-4-difluoromethyl-thiazol-2-yl)-2H-tetrazolium bromo nitrite salt As shown in Scheme 1, o-nitrophenol is reacted with 3-bromo propyltrimethylammonium bromide to form 3-(2-nitrophenoxy)propyltrimethylammonium bromide, which is then hydrogenated to the equivalent aniline. The aniline is reacted with a hydrazone containing a substituted thiazolyl ring and a phenyl ring with a methylene dioxy substituent to produce the formazan. The formazan is then oxidized to the tetrazolium salt. The process is more completely described in the following example: To a yellow solution of o-nitrophenol (Aldrich, 6.3 g, 45 mmol) in DMF (150 mL) in a dry 250 mL, one neck, round bottom flask under nitrogen was added potassium carbonate (6.6 g, 48 mmol). The mixture turned orange. After stirring 10 min, 3-bromopropyltrimethylammonium bromide (Aldrich, 12.9 g, 45 mmol) was added. The resulting mixture was heated at 125° C. for 3 hrs. After cooling the reaction mixture to room temperature, the residue was filtered and the precipitate was washed with DMF (2×2Ø mL). The filtrate was slowly added to EtOAc (750 mL) causing a precipitate to form. The resulting mixture was stirred 30 min. The precipitate was filtered and washed with a solution of EtOAc:DMF, 5:1 (3×100 mL), then EtOAc (100 mL) and Hexane (100 mL). After air-drying the light yellow solid for 5 min, the product was added to a solution of EtOAc:DMF, 10:1 (550 mL) and stirred 1 hr. The solid was filtered, washed with EtOAc (100 mL) and Hexane (100 mL). The resulting solid was filtered to yield a light beige product (14.54 g,>100%), mp (178°-181° C.) identified by the following properties. $^{13}C$ NMR (400 MHz, DMSO $d_6$): δ 151, 139.45, 134.71, 125.14, 121, 115.39, 66.59, 62.84, 52.39, 22.48 $^1H$ NMR (400 MHz, DMSO-$d_6$): δ 7.90 (dd, J=8.1 Hz, J=1.7 Hz, 1H), 7.58 (dt, J=8.2 Hz, J=1.7 Hz, 1H), 7.39 (d, J=8.2 Hz, 1H), 7.15 (d, J=1.7 Hz, 1H), 4.25 (t, J=6 Hz, 2H), 3.45 (m, 2H), 3.11 (s, 9H), 2.23 (m, 2H). ESI-MS: m/z 239 (100%, $M^{2+}$).

A slurry of 3-(2-nitrophenoxy)propyltrimethylammonium bromide (7 g, 21.94 mmol), 10% Pd/C (725 mg), MeOH (70 mL) and water (70 mL) was hydrogenated at 35 psi for 2.5 hrs. in a Parr Hydrogenation apparatus. After 30 min, the pressure dropped to 22 psi. The resulting mixture was filtered through a pad of 521 Celite. The pad of black catalyst/Celite was washed with MeOH (2×10 mL). The filtrate was concentrated on a rotary evaporator tinder reduced pressure at 40-45° C. When there was no further distillate formed, the light pink solution was transferred to another flask and concentrated by freeze-drying for 2 days to yield a light beige aniline derivative (5.92 g, 93%) identified by the following spectral properties. $^{13}C$ NMR (400 MHz, DMSO-$d_6$): δ 145.19, 137.76, 121.39, 116.15, 114.09, 111.86, 64.79, 63.27, 52.36, 22.78 $^1H$ NMR (400 MHz, DMSO-d6): δ 6.78 (d, J=4 Hz, 1H), 6.66 (m, 2H), 6.53 (d, J=6 Hz, 1H), 4.82 (br s, 2H), 3.99 (t, J=6 Hz, 2H), 3.54 (m, 2H), 3.11 (s, 9H), 2.17 (m, 2H). ESI-MS: m/z 209 (100%, $M^{2+}$).

To a solution of the above aniline derivative (7.7 g, 26.64 mmol) in water (80 ml) in an ice water bath was added conc HCl (7.2 ml) dropwise. After the solution was stirred 5 min, a solution of sodium nitrite (2.2 g, 32 mmol) in water (16 mL) was added dropwise. The color of the solution changed from a light brown to a golden yellow. The resulting solution was stirred 30 min. A solution of hydrazone (Bayer, 9.8 g, 27.98 mmol) in pyridine (400 mL) was stirred in a 3 necked 2 liter flask equipped with a mechanical stirrer and jacketed addition funnel in a salt/ice/water bath (−15° to −20° C.). The diazo solution just made was added dropwise to the hydrazone solution via a jacket addition funnel filled with ice/water. After the first few drops, the reaction color changed from yellow to dark blue. After 1/3 addition, the dark blue reaction mixture became very viscous. When the addition was complete, the mixture was stirred 30 min. Then the reaction was warmed to 3-5° C. via an ice/water bath. The reaction was stirred 1 hr. The mixture was transferred to a 2-liter round-bottom flask with MeOH (500 mL). The mixture was concentrated on a rotary evaporator under reduced pressure at 45° C. until no further distillate formed. MeOH (500 mL) again was added and the mixture was concentrated. The process was repeated. The resulting solid was dried under vacuum overnight. Then, the flask was rinsed with MeOH (100 mL) and was diluted with EtOAc (500 mL). The slurry was stirred in an ice/water bath for 30 min. The product was filtered and washed with EtOAc (100 mL), cold MeOH (50 mL), EtOAc (150 mL) and Hexane (150 mL). The resulting dark blue product was transferred to an amber bottle and dried under vacuum to give the desired formazan (13, 11.3 g, 67%) identified by the following spectral properties. $^{19}F$ NMR: (376 mHz, DMSO $d_6$): δ −177.77 (d, J=59.2 Hz), $^{13}C$ NMR (400 MHz, DMSO-$d_6$): δ 169.57, 153.6, 148.1, 147.8, 144.81, 141.9, 137.1, 132.74, 128.82, 121.53, 121.5, 121.1, 115.89, 113.96, 108.8, 108.22, 106.68, 101.33, 66.21, 63.03, 51.99, 22.35 $^1H$ NMR (400 MHz, DMSO-$d_6$): δ 11.78 (br s, 1H), 8.05 (dd, J=8.1 Hz, J=1.5 Hz, 1H), 7.55 (dd, J=8.2 Hz, J=1.6 Hz, 1H), 7.48 (dd, J=8.2 Hz, J=1.7 Hz, 1H), 7.43 (d, J=1.7 Hz, 1H), 7.32 (dd, J=8 Hz, J=<1 Hz, 1H), 7.16 (t, J=7.9 Hz, 1H), 7.15 (t, $J_{HF}$=59.2, 1H), 7.04 (d, J=8.2 Hz, 1H), 6.11 (s, 2H), 4.32 (t, J=6 Hz, 2H), 3.49 (m, 2H), 3.05 (s, 9H), 2.38 (m, 2H). ESI-MS: m/z 611 (100%, M-Ms), 258 (26%, $M^{2+}$).

To a mixture of the above formazan (2.16 g, 3.4 mmol), water (1.4 mL) and THF (40 mL), was added methanesulfonic acid (0.68 mL, 10.24 mmol). The mixture was stirred 5 min. Then sodium nitrite (720 mg, 10.24 mmol) was added in one portion. The mixture was stirred for 3 days. The slurry color changed from dark blue to orange. The orange ppt was filtered and washed with THF (2×10 mL). The product was dried overnight under vacuum. Then the solid was slurried with MeOH (80 mL), filtered and the residue was washed with MeOH (2×5 mL). The filtrate was concentrated on a rotary evaporator under reduced pressure at 40° C. The resulting product was dried 2 days under vacuum to give an orange tet salt (2.86 g>100%) identified by the following spectral properties. $^{19}F$ NMR: (376 MHz, DMSO-$d_6$): δ-181.13 (d, J=52.1 Hz), $^{13}C$ NMR (400 MHz, DMSO-$d_6$): δ 165.1, 152.52, 152.27, 148.85, 146.68, 142.72, 142.45, 137.07, 135.95, 128.44, 123.87, 121.87, 121.86, 121.39, 115.57, 114.68, 110.80, 109.84, 108.43, 107.14, 106.06, 102.78, 100.49, 66.92, 62.23, 52.21, 22.08 $^1H$ NMR (400 MHz, DMSO-$d_6$): δ 7.98 (dd, J=8.0 Hz, J=1.5 Hz, 1H), 7.91 (m, 2H), 7.82 (d, J=1.8 Hz, 1H), 7.53 (d, J=8.2 Hz, 1H), 7.37 (m, 1H), 7.31 (d, J=8.2 Hz, 1H), 7.25 (t, $J_{HF}$=59.2, 1H), 6.27 (s, 2H), 4.17 (t, J=6 Hz, 2H), 3.49 (m, 2H), 2.93 (2, 9H), 2.02 (m, 2H). ESI-MS: m/z 663 (22%, $M^{2+}$+TFA), 645 (17%, $M^+$), 275 (100%, $M^{2+}$).

EXAMPLE 2

Preparation of 5-Benzo[1,3 dioxol-5-yl]-3-[2-(3-trimethylammonium) propoxy-phenyl]-2-(5-chloro-4-difluoromethyl-thiazol-2-yl)-2 H-tetrazolium bromo tetrafluoroborate salt Salt was prepared as Ex. 1 except to use 48% tertahydrofluoroboric acid with the same formazan to yield the desired orange tetrazolium salt. $^{13}C$ NMR (400 MHz, DMSO $d_6$): 6137, 128, 124, 121, 114, 111, 110, 108, 107, 106, 103, 68, 63, 53, 28 $^{19}F$ NMR: (376 MHz, DMSO-$d_6$): δ-181.13 (d, J=59.2 Hz), $^1H$ NMR (400 MHz, DMSO-$d_6$): δ 7.92 (m, 3H), 7.82 (d, J=1.8 Hz, 1H), 7.52 (bd, J=8.2 Hz, 1H), 7.37 (m, 1H), 7.31 (d, J=8.2 Hz, 1H), 7.25 (t, $J_{HF}$=59.2 Hz, 1H), 6.27 (s, 2H), 4.17 (t, J=6 Hz, 2H), 3.35 (m, 2H), 2.93 (2, 9H), 2.02 (m, 2H). ESI-MS: m/z 637 (100%, $M^+$-Br).

EXAMPLE 3

Preparation of 5-Benzo[1,3 dioxol-5-yl]-3-[2-(3-dimethylhydrogenammoniun) propoxy-phenyl]-2-(5-chloro-4-difluoromethyl-thiazol-2-yl)-2 H-tetrazolium bromo nitrite salt To a yellow solution of o-nitrophenol (Aldrich, 2.1 g, 45 mmol) in DMF (50 mL) in a dry 100 mL, one neck, round bottom flask under nitrogen was added potassium carbonate (4.4 g, 32 mmol). The mixture turned orange. After stirring 10 min, 3-chloropropyldimethylammonium hydrogen chloride (Aldrich, 2.4 g, 16.5 mmol) was added. The resulting mixture was heated at 125° C. one day. After cooling the reaction mixture to room temperature, the residue was filtered and the precipitate was washed with MeOH (2×10 mL). The filtrate was concentrated under vacuum at 40° C. until 5 mL. Then EtOAc (100 mL) was added. A ppt. formed and was filtered. Water (100 mL) and EtOAc (150 mL) was added to the filtrate, layers mixed and separated. The aqueous layer was extracted with EtOAc (3×25 mL). The combined EtOAc extracts were washed with saturated aqueous sodium chloride (25 mL), dried over magnesium sulfate (5 g), filtered and concentrated to give a yellow oil (2.55 g, 81%). $^1$H NMR (400 MHz, DMSO-$d_6$): δ 7.80 (dd, J=8.1 Hz, J=1.7 Hz, 1H), 7.58 (dt, J=8.2 Hz, J=1.7 Hz, 1H), 7.05 (d, J=8.2 Hz, 1H), 6.65 (d, J=1.7 Hz, 1H), 4.25 (t, J=6 Hz, 2H), 2.45 (m, 2H), 2.15 (s, 9H), 1.9 (m, 2H). ESI-MS: m/z 225 (100%, M+1).

The alkylated nitrophenol was treated in the same fashion as in Example 1 to yield the desired tet salt. $^{13}$C NMR (400 MHz, DMSO $d_6$): δ 127, 124, 121, 115, 110, 109, 108, 107, 104, 102, 64, 48, 36, 28 $^{19}$F NMR: (376 MHz, DMSO-$d_6$) (d, J=59.2 Hz): δ-119.13, $^1$H NMR (400 MHz, DMSO-$d_6$): δ 7.95 (m, 3H), 7.80 (d, J=1.8 Hz, 1H), 7.50 (d, J=8.2 Hz, 1H), 7.35 (t, J=8.2 Hz, 1H),), 7.31 (d, J=8.2 Hz, 1H), 7.25 (t, $J_{HF}$=59.2, 1H), 6.27 (s, 2H), 4.20 (t, J=6 Hz, 2H), 3.45 (m, 2H), 2.65 (d, j=1.8 Hz, 6H), 1.98 (m, 2H). ESI-MS: m/z 535 (100%, M$^{2+}$).

EXAMPLE 4

Preparation of 5-Benzo[1,3 dioxol-5-yl]-3-[2-(3-trimethylammonium) propoxy-phenyl]-2(benzothiazol-2-yl)-2 H-tetrazolium bromo nitrite salt The piperonal-benzothiazol-2-yl hydrazone was reacted with the 3-(2-aminophenoxy) propyltrimethyl ammonium bromide as in Example 1 to make the formazan, which was then converted to the corresponding tetrazolium salt.

Piperonal benzothiazol-2-yl hydrazone (Bayer, 2.5 g, 10.5 mmol) was reacted with the aniline derivative from example 1 (2.85 g, 9.6 mmol) under similar conditions as used in making the formazan in Example 1 to give a dark purple solid. (4.7 g, 82%) identified by the following spectral properties. $^1$H NMR (400 MHz, DMSO-$d_6$): δ 11.78 (br s, 1H), 7.98 (dd, 2H), 7.73 (m, 1H), 7.60 (m, 2H), 7.50 (m, 1H), 7.41 (m, 2H), 7.29 (m, 1H), 7.05 (d, 1H), 6.14 (s, 2H), 4.39 (t, 2H), 3.55 (m, 2H), 3.05 (s, 9H), 2.48 (m, 2H). ESI-MS: m/z 517 (100%, M$^+$).

Above formazan (600 mg, 1.01 mmol) was converted to tetrazolium salt (870 mg, >100%) under the same conditions in Example 1. The tetrazolium salt was identified by the following spectral properties. $^{13}$C NMR (100 MHz, DMSO-$d_6$): δ 164.98, 152.59, 152.26, 148.91, 136.64, 132.74, 135.08, 129.27, 128.88, 128.24, 124.77, 123.97, 123.7, 122.6, 121.97, 115.81, 114.56, 109.86, 107.12, 102.82, 66.88, 62.26, 52.2, 22.02. $^1$H NMR (400 MHz, DMSO-$d_6$): δ 8.42 (dd, J=8.2 Hz, J=0.8 Hz, 1H), 8.03 (dd, J=7.7 Hz, J=1.6 Hz, 1H), 8.02 (dd, J=8.1 Hz, J=0.9 Hz, 1H), 7.97 (dd, J=8.2 Hz, J=1.8 Hz, 1H), 7.93 (m, 1H), 7.86 (d, J=1.7 Hz, 1H), 7.76 (m, 1H), 7.73 (m, 1H), 7.55 (dd, J=8.6 Hz, J=0.9 Hz, 1H), 7.39 (m, 1H), 7.32 (d, J=8.1 Hz, 1H), 6.28 (s, 2H), 4.12 (t, J=6 Hz, 2H), 3.16 (m, 2H), 2.91 (s, 9H). ESI-MS: m/z 561.2 (100%, M$^+$).

EXAMPLE 5

Preparation of 5-Benzo[1,3 dioxol-5-yl]-3-[2-(3-trimethylammonium) propoxy-phenyl]-2-(6-methoxynapthylthiazol-2-yl)-2 H-tetrazolium bromo nitrite salt 6-Methoxy-2-hydrazino-napthylthiazole was used instead of 2-hydrazino-benzothiazole in Ex. 4 to make the appropriate hydrazone. Then the hydrazone was subjected to the same conditions to yield the desired formazan (44% overall) $^{13}$C NMR (400 MHz, DMSO-$d_6$): δ 135, 130, 125, 122, 121, 120, 115, 114, 113, 110, 65, 64, 55, 52, 38, 22 $^1$H NMR (400 MHz, DMSO-$d_6$): δ 8.61 (d, J=8.1 Hz, 1H), 8.29 (d, J=8.2 Hz, 1H), 8.05 (dd, J=8.1 Hz, J=1.8 Hz, 1H), 7.82 (dt, J=8.2 Hz, J=1.7 Hz, 1H), 7.68 (m, 2H), 7.61 (dd, J=8.1 Hz, J=1.6 Hz, 1H), 7.55 (d, J=1.8 Hz), 7.37 (dd, J=8.2 Hz, J=1.8 Hz, 1H), 7.31 (dd, J=8.2 Hz, J=1.8 Hz, 1H), 7.27 (dt, J=8.1 Hz, J=1.7 Hz, 1H), 7.08 (d, J=8.1 Hz, 1H), 6.12 (s, 2H), 4.45 (t, J=6 Hz, 2H), 4.10 (s, 3H), 3.60 (m, 2H), 2.95 (s, 9H), 2.65 (m, 2H). ESI-MS: m/z 597 (100%, M$^+$).

To a solution of acetic acid (5 mL) and tetrahydrofuran (5 mL) in an ice/salt/water bath, was added sodium nitrite (143 mg, 2.08 mmol). After stirring 10 min, the above formazan (340 mg, 0.051 mmol) was added. After 1 hr, the reaction was allow to warm to rt and stirred overnight. The dark maroon mixture was filtered and the solid was washed with acetic acid (3×5 mL), ethyl acetate (2×10 mL) and hexane (10 mL). The filtrate was concentrated on the rotary evaporator at 30° C. then dried overnight under vacuum. The residue was slurried with ethyl acetate (15 mL), settled and decanted. This process was repeated. Then hexane (10 mL) was added. The product was filtered and dried overnight to give the desired maroon tet salt (260 mg, 75%) $^{13}$C NMR (400 MHz, DMSO-$d_6$): δ 129, 128, 126, 123, 121, 119, 115, 114, 112, 108, 105, 101, 98, 66, 63, 57, 51, 22 $^1$H NMR (400 MHz, DMSO-$d_6$): δ 8.32 (m, 1H), 8.02 (m, 4H), 7.87 (d, J=1.8 Hz, 1 Hz), 7.78 (m, 3H), 7.66 (d, 8.2 Hz, 1H), 7.47 (t, J=8.2 Hz, 1H), 7.33 (d, J=8.2 Hz, 1H), 6.28 (s, 2H), 4.13 (s, 3H), 3.15 (m, 2H), 2.85 (s, 9H), 1.87 (m, 2H). ESI-MS: m/z 298 (100%, M$^{2+}$), 709 (20%, M$^+$+TFA).

EXAMPLE 6

Preparation of 5-[4-(3-trimethylammonium) propoxy-3-methoxy-phenyl]-3-[2-(3-trimethylammonium) propoxy-phenyl]-2-(5-chloro-4-difluoro methyl-thiazol-2-yl)-2H-tetrazolium dibromo nitrite salt 4-hydroxy-3-methoxybenzaldehyde was reacted with 3-bromopropyltrimethylammonium bromide to introduce another trimethylammoniumpropoxy substituent. The product was reacted with 5-chloro-4-difluoromethyl-2-hydrazino-thiazole to produce a hydrazone. The hydrazone is reacted with the 3-(2-aminophenoxy) propyltrimethylammonium bromide as described in Example 1 to produce the formazan, which is converted to the corresponding tetrazolium salt. 4-hydroxy 3 methoxy-benzaldehyde (Vanillin, Aldrich, 4.56 g, 30 mmol) was alkylated with 3-bromopropyl trimethylammonium bromide (8.8 g, 34 mmol) under the same conditions as used in Example 1 to prepare an off-white product (9.73 g, 97%) identified by the following spectral properties. $^{13}$C NMR (400 MHz, DMSO-$d_6$): δ 192.5, 155, 150, 130, 125.75, 112.6, 110, 66.5, 63.4, 56, 25.5. $^1$H NMR (400 MHz, DMSO-$d_6$): δ 9.88 (s, 1H), 7.58 (dd, J=8.2 Hz, J=1.9 Hz, 1H), 7.41 (d, J=1.9 Hz, 1H), 7.22 (d, J=8.2 Hz, 1H), 4.35 (t, J=6.4 Hz, 2H), 3.49 (m, 2H), 3.14 (s, 9H), 2.30 (m, 2H). ESI-MS: m/z 252.2 (100%, M$^+$).

To a slurry of the above alkylated benzaldehyde (6.8 g, 20.5 mmol) and 5-chloro-4-difluoro methyl-2-hydrazino-thiazole (Bayer, 3.72 g, 18.6 mmol) in MeOH (60 mL) was added acetic acid (0.55 mL). The slurry almost dissolved after 5 min. The resulting mixture was heated at 80° C. overnight. After cooling the reaction to room temperature, the solution was slowly added to EtOAc (650 mL). A light grey precipitate formed. The mixture was stirred for 30 min. The solid was filtered and washed with EtOAc and hexane. The light grey product was transferred to an amber bottle and dried under vacuum overnight to give the desired hydrazone (8.7 g, 87%) identified by the following properties. $^{19}$F NMR: (376 MHz, DMSO-$d_6$): δ 111.08 (d, J=47 Hz), $^{13}$C NMR (400 MHz, DMSO-$d_6$): δ 143, 121, 114, 109, 108.5, 66, 63, 55, 53, 39, 22. $^1$H NMR (400 MHz, DMSO-$d_6$): 12.37 (s, 1H), 7.29 (d, J=1.9 Hz, 1H), 7.19 (dd, J=10 Hz, J=1.8 Hz, 1H), 7.06 (t J=7.7 Hz, 1H), 7.18 (m, 1H), 6.95 (t, $J_{HF}$=47, 1H), 4.09 (t, J=6.1 Hz, 2H), 3.83 (s, 3H), 3.47 (m, 2H), 3.47 (m, 2H), 3.29 (s, 9H), 2.50 (m, 2), 2.20 (m, 2H). ESI-MS: m/z 433.1 (100%, M$^+$).

The above hydrazone (7.08 g, 13.86 mmol) was reacted with aniline derivative from Example 1 (6 g, 20.76 mmol) under similar conditions as Example 1 to give a dark blue formazan (8.56 g, 76%) identified by the following spectral properties. $^{19}$F NMR: (376 MHz, DMSO-$d_6$): δ 177.77 (d, J=59.2 Hz) $^{13}$C NMR (400 MHz, DMSO-$d_6$.): δ 153, 148.98, 148.63, 144.5, 136.5, 132.73, 132.74, 127, 121.59, 119.53, 115.54, 113.96, 113.58, 110.98, 108.92, 66.10, 65.79, 62.77, 55.54, 52.15, 22.45, 22.25. $^1$H NMR (400 MHz, DMSO-$d_6$): δ: 11.78 (br s, 1H), 8.03 (dd, J=8.5 Hz, J=1.5 Hz, 1H), 7.56 (m, 1H), 7.52 (dt, J=8.5 Hz, J=2 Hz, 1H), 7.50 (d, J=2 Hz, 1H), 7.35 (dd, J=8.5 Hz, J=1.5 Hz, 1H), 7.30 (d, J=7.9 Hz, 1H), 7.18 (m, 1H), 7.17 (t, $J_{HF}$=59.2, 1H), 4.35 (t, J=5.8 Hz, 2H), 4.13 (t, J=6.1 Hz, 2H), 3.88 (s, 3H), 3.55 (m, 2H), 3.50 (m, 2H), 3.14 (s, 9H), 3.07 (s, 9H), 2.50 (m, 2H), 2.30 (m, 2H). ESI MS: m/z 652.2 (45%, M$^+$), 326.8 (100%, M$^+$).

Above formazan (2.44 g, 3 mmol) was converted to the tetrazolium salt under similar conditions as used in Example 1 except that the reaction mixture was heated at 40° C. for 15 hrs. The product was identified by the following spectral properties. $^{13}$C NMR (100 MHz, DMSO-$d_6$): δ 136.7, 128.5, 121.9, 121.8, 114.5, 113.5, 110.2, 108.1, 105.7, 66.7, 66.1, 62.5, 62.1, 56.1, 52.1, 51.8, 21.8, 21.2. $^1$H NMR (400 MHz, DMSO-$d_6$): δ 8.06 (dd, J=8.1 Hz, J=1.5 Hz, 1H), 7.93 (m, 8H), 7.77 (d, J=2 Hz, 1H), 7.53 (d, J=8.6 Hz, 1H), 7.38 (t, J=8.5 Hz, 2H), 7.26 (d, J=52.2 Hz, 2H), 4.23 (t, J=6H, 2H), 4.17 (t, J=6.1 Hz, 2H), 3.94 (s, 3H), 3.53 (m, 2H), 3.32 (m, 2H), 3.14 (s, 9H), 3.01 (s, 9H), 2.26 (m, 2H), 2.03 (m, 2H), ESI MS: m/z 652.2 (45%, M$^+$), 326.8 (100%, M$^+$), 326.8 (100%, M$^{2+}$).

EXAMPLE 7

Preparation of 5-[4-(3-trimethylammonium) propoxy-3-methoxy-phenyl])-3-[2-(3-trimethylammonium)propoxy-phenyl]-2-(6-ethoxy-benzothiazol-2-yl)-2H-tetrazolium dibromo nitrite salt 6-Ethoxy-2-hydrazino-benzothiazole was reacted with the alkylated benzaldehyde made as in Example 6 to form a hydrazone, which is then reacted with the substituted aniline as made in Example 1 to make the formazan. The formazan was converted to the equivalent tetrazolium salt.

6-Ethoxy-2-hydrazino-benzothiazole (Acros, 4.62 g, 22 mmol) was reacted with 4-(3-trimethylammonium propoxy)-3-methoxy-benzaldehyde under similar conditions as in Example 6 to give a light grey product (10.23 g, 95%) identified by the following properties.

$^{13}$C NMR (400 MHz, DMSO-$d_6$): δ 165.58, 153.82, 153.74, 149.24, 148.96, 142.42, 128.01, 120.16, 118.24, 113.62, 113.54, 108.66, 106.49, 101.33, 65.83, 63.51, 62.86, 55.32, 52.16, 22.51, 14.6. $^1$H NMR (400 MHz, DMSO-$d_6$): δ 11.98 (br s, 1H), 8.03 (s, 1H), 7.38 (d, J=2.2 Hz, 1H), 7.34 (d, J=8.7 Hz, 1H), 7.32 (d, J=1.8 Hz, 1H), 7.20 (dd, J=8.4 Hz, J=1.8 Hz, 1H), 7.07 (d, J=8.4 Hz, 1H), 6.89 (dd, J=8.7 Hz, J=2.5 Hz, 1H), 4.09 (t, J=6.1H, 2H), 4.03 (t, J=7 Hz, 2H), 3.84 (m, 3H), 3.49 (m, 2H), 3.12 (s, 9H), 2.22 (m, 2H), 1.33 (t, J=7 Hz). ESI-MS: m/z 561.2 (100%, M$^+$). ESI-MS: m/z 443.1 (78%, M$^+$), 222.1 (100%, M$^{+2}$).

The hydrazone prepared above (3.6 g, 6.93 mmol) was reacted with aniline from Example 1, (3 g, 10.38 mmol) under similar conditions as used in Example 1 to prepare formazan except using a 3:1 mixture of pyridine and DMF as a solvent to give the desired dark blue product (3.8 g, 66%) identified by the following spectral properties. $^{13}$C NMR (400 MHz, DMSO-$d_6$): δ 130.5, 123.2, 121.8, 118.8, 116, 115.3, 114.1, 113.8, 109.8, 106.3, 67.1, 66.5, 63.6, 52.5, 22.6, 22.5, 14.2. $^1$H NMR (400 MHz, DMSO-$d_6$): δ 11.78 (br s, 1H), 8.01 (br d, J=8 Hz, 1H), 7.81 (br s, 1H=8.8 Hz, 1H), 7.62 (m, 3H), 7.48 (t, J=8 Hz, 1H), 7.33 (d, J=8.3 Hz, 1H), 7.16 (m, 1H), 7.10 (dd, J=8.8 Hz, J=2.4 Hz, 1H), 4.38 (t, J=5.8 Hz, 2H), 4.13 (m, 2H), 3.91 (s, 3H), 3.55 (m, 2H), 3.50 (m, 2H), 3.13 (s, 9H), 3.08 (s, 9H), 2.54 (m, 2H), 2.25 (m, 2H), 1.38 (t, J=7 Hz, 3H). ESI MS: m/z 776 (12%, M$^{+}$+TFA) 662.2 (45%, M$^+$), 331.8 (100%, M$^{+2}$).

Above formazan (1.24 g, 1.5 mmol) was converted to the tetrazolium salt (2 g, >100%) under similar conditions as used in Example 1. The product was identified by the following spectral properties. $^{13}$C NMR (400 MHz, DMSO-$d_6$): δ 136.8, 128.1, 125.4, 121.5, 121.4, 114, 113.5, 109.8, 106.8, 66.6, 66.2, 64.5, 62.5, 62.2, 56.1, 52.2, 52.1, 22.1, 21.5, 13.5. $^1$H NMR (400 MHz, DMSO-$d_6$): δ 8.04 (dd, J=8 Hz, J=1.5 Hz, 1H), 7.95 (m, 4H), 7.78 (d, J=2 Hz, 3H), 7.54 (d, J=8.5 Hz, 1H), 7.40 (t, J=7.8 Hz, 1H), 7.38 (d, J=8.6 Hz, 1H), 4.23 (t, J=6.1H, 2H), 4.1 (q, J=8 Hz, 2H), 4.12 (m, 2H), 3.96 (s, 3H), 3.53 (m, 2H), 3.50 (m, 2H), 3.18 (m, 2H), 3.15 (s, 9H), 2.92 (2, 9H), 2.30 (m, 2H), 1.89 (m, 2H), 1.40 (t, J=7 Hz, 2H). ESI MS: m/z 220.8 (100%, M$^{+3}$).

EXAMPLE 8

Preparation of 5-[4-(3-trimethylammonium)propoxy-3-methoxy-phenyl]-3-[2-(3-trimethylammonium)propoxy-phenyl]-2-(6-bromo-benzothiazol-2-yl)-2H-tetrazolium dibromo nitrite salt 6-Bromo-2-hydrazino-benzothiazole was used instead of 6-Ethoxy-2-hydrazino-benzothiazole in Ex. 8 to make the appropriate hydrazone. Then the hydrazone was subjected to the same conditions to yield the desired formazan (44% overall) $^1$H NMR (400 MHz, DMSO-$d_6$), δ 7.90 (dd, J=8.1 Hz, J=1.7 Hz, 1H), 7.58 (dt, J=8.2 Hz, J=1.7 Hz, 1H), 7.39 (d, J=8.2 Hz, 1H), 7.15 (d, J=1.7 Hz, 1H), 4.25 (t, J=6 Hz, 2H), 3.45 (m, 2H), 3.11 (s, 9H), 2.48 (m, 2H), 2.25 (m, 2H). ESI-MS: m/z 249 (100%, M$^{2+}$).

The formazan (322 mg, 0.375 mmol) was subjected to the same condition in Example 8 to form the tetrazolium salt except that reaction was heated at 40° C. overnight to yield the desired tetrazolium salt (478 mg,>100%). $^{13}$C NMR (100 MHz, DMSO d$_6$): δ 151, 139.45, 134.71, 125.14, 121, 115.39, 66.59, 62.84, 52.39, 22.48: δ 7.90 $^1$H NMR (400 MHz, DMSO-d$_6$), 8.74 (d, J=2.1 Hz, 1H), 7.95 (m, 5H), 7.78 (d, J=2.1 Hz, 1H), 7.51 (d, J=7.8 Hz, 1H), 7.39 (m, 2H), 4.2 (m, 2H), 4.08 (m, 2H), 3.96 (s, 3H), 3.53 (m, 2H), 3.19 (m, 2H), 3.11 (s, 9H), 2.91 (s, 9H), 2.24 (m, 2H), 1.87 (m, 2H). ESI-MS: m/z 233 (100%, M$^{3+}$).

EXAMPLE 9

Preparation of 5-[4-(3-trimethylammonium) propoxy-3-methoxy-phenyl]-3-[2-(3-trimethylammonium) propoxy-phenyl]-2-(6-ethoxy-benzothiazol-2-yl)-2H-tetrazolium tribromide salt To a slurry of formazan (from Ex. 7, 1.18 gr, 1.43 mmol) in acetonitrile (15 mL) was added n-bromosuccinimide (300 mg, 1.69 mmol) at room temperature. After 1 hr, everything dissolved. After 3 hr, an orange ppt formed. Stirred reaction overnight. Ppt was filtered and wash with acetonitrile (3×5 mL). The resulting orange product was dried overnight under vacuum. (1.07 g, 83%) $^{13}$C NMR (100 MHz, DMSO d$_6$): δ 151, 139.45, 134.71, 125.14, 121, 115.39, 66.59, 62.84, 52.39, 22.48 $^1$H NMR (400 MHz, DMSO-d$_6$): δ 8.08 (d, J=8.2 Hz, 1 H), 8.04 (d, J=1.7 Hz, 1H), 7.94 (m, 3H), 7.79 (bs, 1H), 7.55 (d, J=8.2 Hz, 1H), 7.40 (d, J=8.2 Hz, 1H), 7.30 (dd, J=8.2 Hz, J=1.7 Hz, 1H), 4.23 (t, J=6 Hz, 2H), 4.15 (q, J=8.2 Hz, 2H), 4.10 (m, 2H), 3.95 (s, 3H), 3.57 (m, 2H), 3.22 (m, 2H), 3.15 (s, 9H), 2.95 (s, 9H), 2.30 (m, 2H), 1.90 (m, 2H), 1.4 (t, J=8.2 Hz). ESI-MS: m/z 221 (100%, M$^{3+}$).

Figure 3:
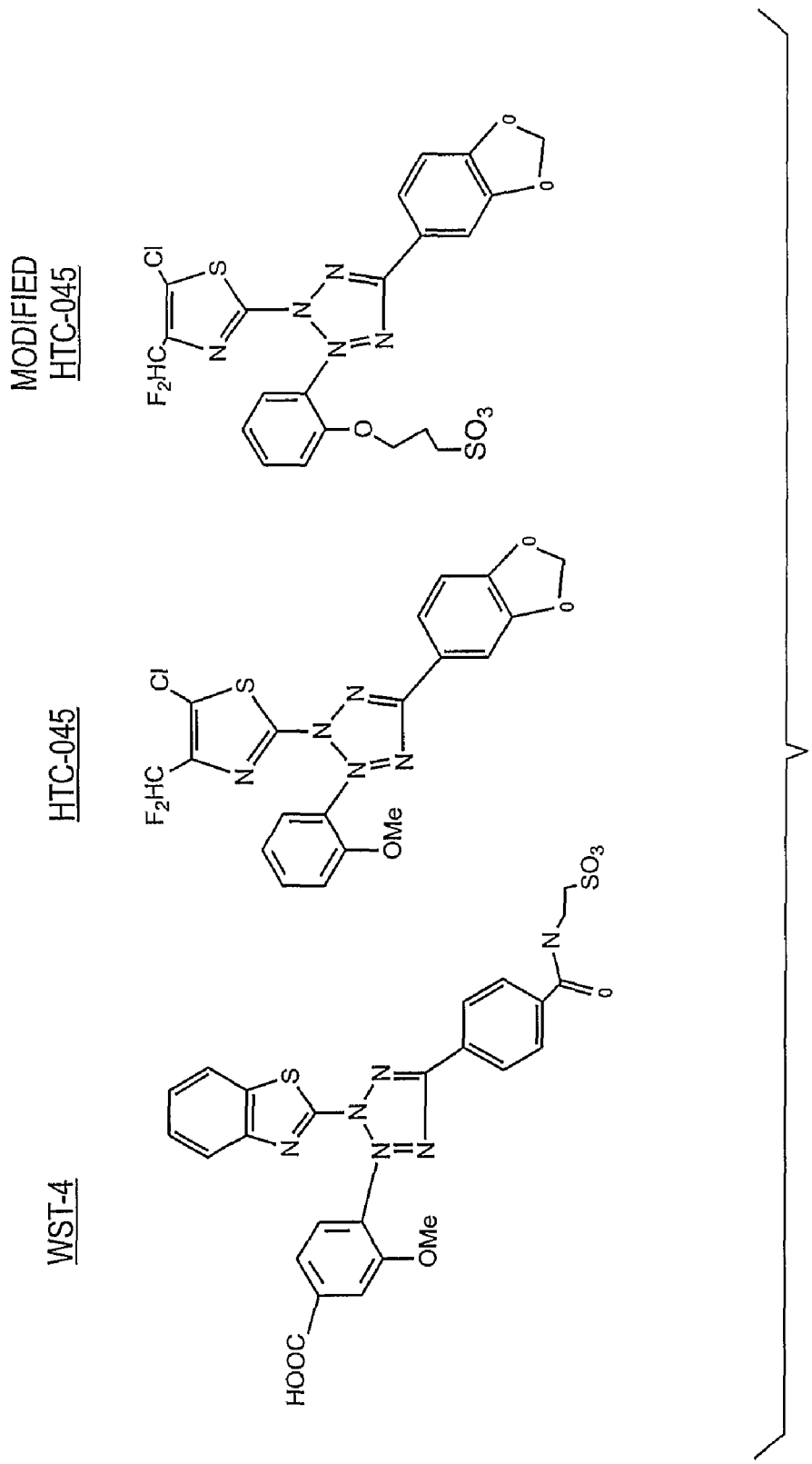
FIG. 3 shows comparative compounds reported in the examples.
Figure 4A:
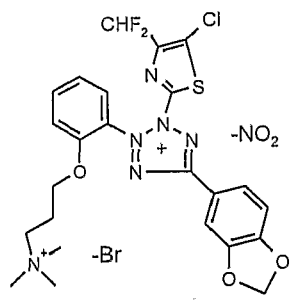
FIGS. 4a-b show compounds of the invention made in the examples.
Figure 4A:
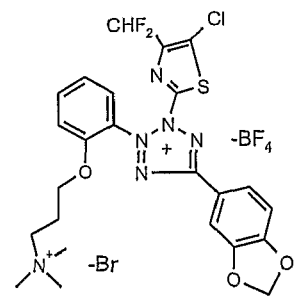
Figure 4A:
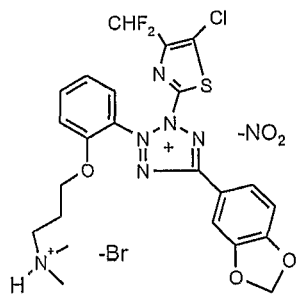
Figure 4A:
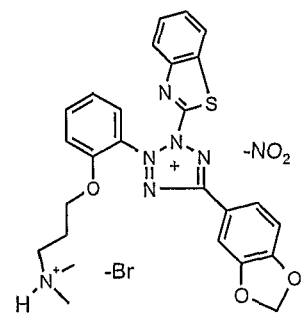
Figure 4A:
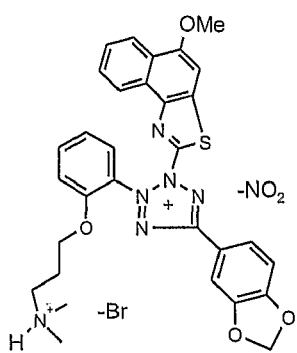
Figure 4A:
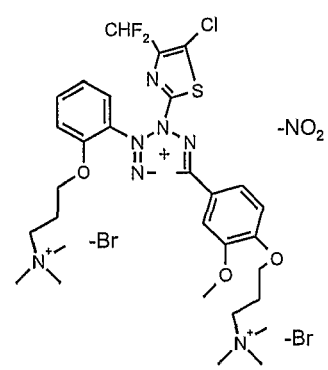
Figure 4B:
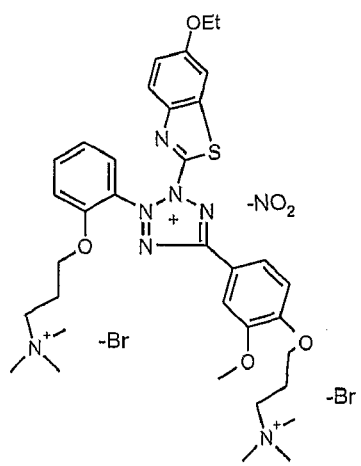
Figure 4B:
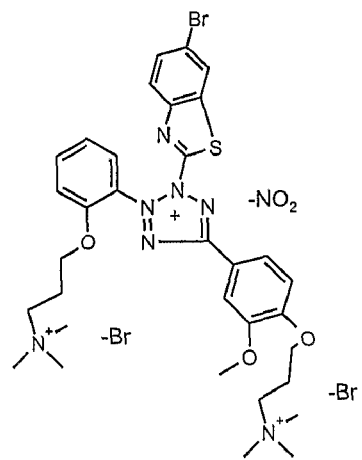
Figure 4B:
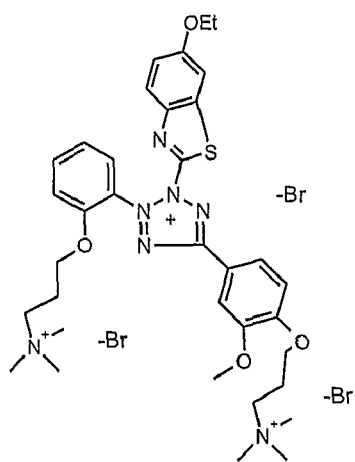

The solubility of the tetrazolium salts made in Examples 1-9 was determined by adding 0.2M phosphate buffer, pH ~7.5, at room temperature to a known amount of each compound until the compound was dissolved. The results are shown in Table 1, where they are compared with WST-4, a thiazolyl tetrazolium salt of Dojindo Laboratories, HTC-045, a thiazolyl tetrazolium salt of Bayer Corp. and a modified HTC-045 where the methoxy group was replaced with a 3-sulfonatepropoxy group (See FIG. 3).

TABLE 1

| Example Number | (Counterion) | Solubilility (mM) |
| --- | --- | --- |
| 1 | (bromo nitrite) | 33 |
| 2 | (bromo tetra fluoroborate) | 5 |
| 3 | (bromo nitrite) | 9 |
| 4 | (bromo nitrite) | 167 |
| 5 | (bromo nitrite) | 5 |
| 6 | (dibromo nitrite) | 181 |
| 7 | (dibromo nitrite) | 169 |
| 8 | (dibromo nitrite) | 290 |
| 9 | (tribromide) | 260 |
| WST-4 | | 118 |
| HTC-045 | | 21 |
| Modified HTC-045 | | 8 |

Although improved solubility of tetrazolium salts has been obtained by adding trialkyl ammonium propoxy substituents to thiazolyl tetrazolium salts, this improvement was not readily predicted, based on prior art. Prior art would predict that the addition of a 3-sulfonatepropoxy group into the molecule would enhance the water-solubility of the molecule. The introduction of a sulfonic acid group into a molecule was used by Dojindo Laboratories. However, the substitution of a 3-sulfonate propoxy group for the methoxy group on the phenyl group attached to the tetrazolium ring (see modified HTC-045 FIG. 3) resulted in a lower solubility, 8 mM than HTC-045 (21 mM). Thus in our molecular structure, this phenomena was not evident. We discovered that a different polar group would improve water solubility. However, other unexpected effects were observed, as will be discussed below.

The substitution of a trimethyl ammonium propoxy group for the methoxy group increased the solubility from 21 mM (HTC-045) to 33 mM (Example 1) and the addition of a second trimethyl ammonium propoxy (Example 6) substantially increased the solubility to 181 mM. However, the solubility was substantially decreased when a tetrafluoro borate counterion was substituted for the nitrate. (Compare Example 2 with Example 1). The solubility of the tetrazolium salt in Example 1 was decreased in Example 3 when the trimethyl ammonium propoxy group was modified to a dimethyl ammonium propoxy group.

The substantial increase in solubility resulting from adding two trimethyl ammonium propoxy groups (Example 6) was also found unexpectedly in Example 4 (167 mM) where only one trimethyl ammonium propoxy group was included, but the substituted thiazoyl group was replaced with an unsubstituted benzothiazoyl group. However, further addition to the thiazoyl group, shown in Example 5 where a substituted naphthyl thiazoyl group was used, was found to have poor solubility (5 mM). In another unexpected result, shown in Example 7, addition of two trimethyl ammonium groups and a benzothiazoyl group, both of which gave significant increases in solubility, appeared to have no complementary effect. Example 7 had a solubility of 167 mM.

Another substantial increase in solubility resulted when the ethoxy group on the benzothiazoyl group of Example 7 was replaced with a bromo group in Example 8. The solubility increased from 169 mM to 290 mM, the highest value shown here. A similar result was found when the counterion in Example 7, the nitrite ion, was replaced by a bromide ion in Example 9. The solubility increased from 169 mM to 260 mM. It appears that including bromine is an effective means of improving solubility of this family of tetrazolium salts.

Figure 5A:
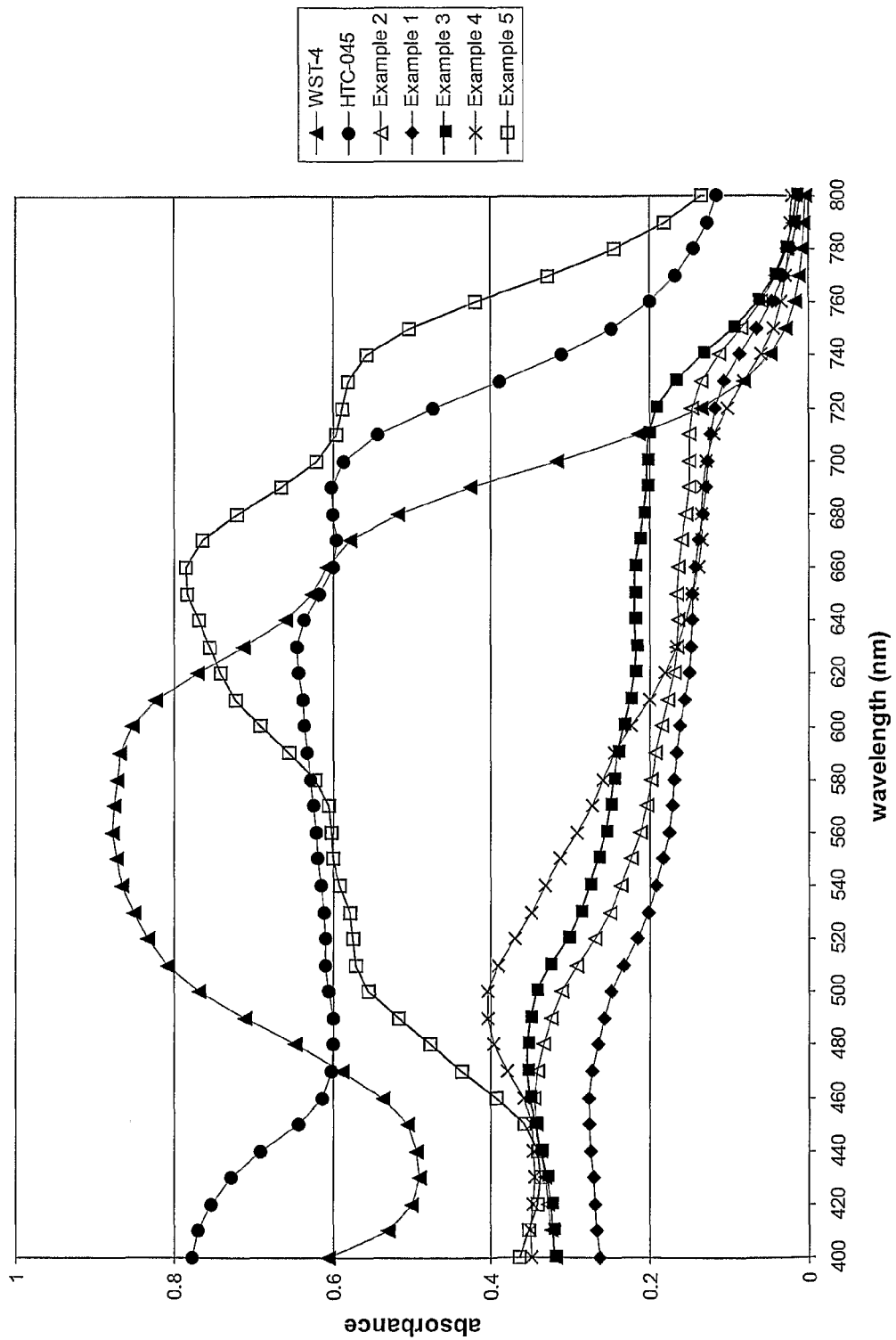
FIGS. 5a and b are plots of tetrazolium salt absorbance versus light wavelength.
Figure 5B:
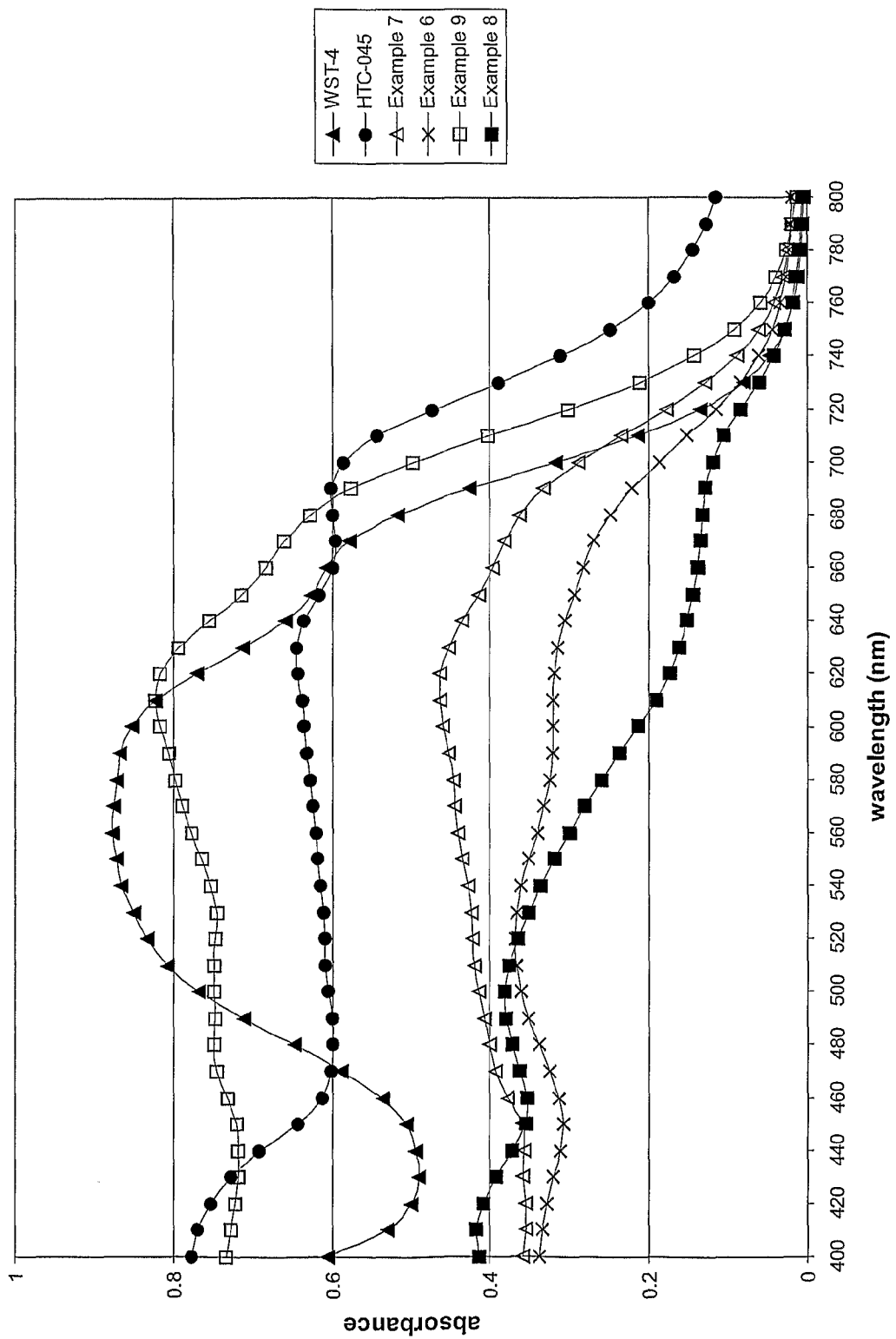

The compounds prepared and tested for their solubility had somewhat different spectral properties. The absorption spectra of each formazan formed from the tetrazolium salt and tested for solubility in Table 1 was measured with a Hewlett Packard Model 8453 diode-array UV-visible spectrophotometer. Solutions of 100 μM of a tetrazolium salt were prepared in 100 mM potassium phosphate buffer. The formazan spectra were measured after the addition of 5-fold excess ascorbate acid salt to convert the tet salts to their formazans. The results are presented in FIGS. 5a and b.

As previously noted, the formazans from thiazolyltetrazolium salts were intended to absorb light at wavelengths above 640 nM, and a flat response was desirable. In both FIGS. 5a and b the absorbance of HTC-045 and WST-4 have been plotted for comparison. While WST-4 demonstrates a peak absorbance in the range of about 560 nM HTC-045 shows a relatively flat absorbance between about 460 nM to 660 nM. Its solubility, however, is lower than WST-4. Adding the trimethyl ammonium propoxy group altered the spectral curves. Examples 1, 2, 3, 4, 6, 7, and 8 have lower absorbance than HTC-045, but the curves are relatively flat throughout the range shown. It appears that the tet salt of Example 5, including a napthyl thiazoyl group not only had low solubility, but showed a rising absorbance verses wavelength curve, demonstrating no flat regions comparable to HTC-045 or the modified compounds of Examples 1, 2, 3, 4, 6, 7, and 8. Example 9 showed a spectral curve having a relatively flat response between 400 and 640 nM as well as being highly soluble.

Ideally, a tetrazolium salt should yield a formazan that has high absorbance within a wide range of wavelengths so that the color developed when an analyte is reacted can be easily and reliably measured. Thus, a relatively flat curve is most desirable. As can be seen from the solubilities of the formazans resulting from the tet salts tested, all of them, with the possible exception of Example 5, show promise as useful indicators. The tetrazolium salt of Example 5 is a novel compound and could be used as an indicator, but it would not be preferred over those having more uniform spectral curves and greater solubility.

Use of Tetrazolium Salts

While tetrazolium salts are useful indicators for many applications, they are particularly valuable when used in test strips used for measuring analytes in biological samples. One important application is in measuring the glucose content of blood.

Test strips typically comprise a carrier and a reagent composition. The reagents, (e.g. glucose dehydrogenase) and a co-factor (e.g., NAD or PQQ), react with the analyte (e.g. glucose) in the biological samples and a mediator (e.g. PMS or the enzyme diaphorase), reduces the thiazolyl tetrazolium salt to its corresponding colored formazan. The resulting color is usually measured most accurately in a meter designed for that purpose. A light source (e.g., an LED), supplies incident light onto the test strip. Light reflected from the test strip is measured by a light detector and correlated with the amount of the analyte that had been reacted.

The thiazolyl tetrazolium indicators of the invention provide the wide spectrum available from the indicators disclosed in U.S. Pat. No. 5,126,275 and others mentioned earlier. But, as shown in the examples, many of the new thiazolyl tetrazolium indicators have improved solubility compared to HTC-045, thereby providing more rapid test times and more accurate results.

The Invention is summarized in the following alternative embodiment.

Alternative Embodiment A

A compound having the formula

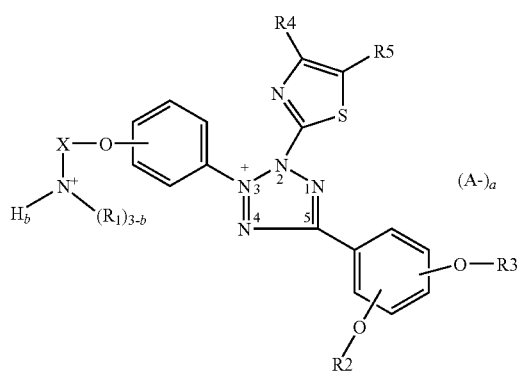

wherein:
A=counter-ion
a=1-3
b=0-3
X=1-6C alkyl or heteroalkyl
$R_1$=1-6C alkyl
one of $R_2$ and $R_3$ is alkyl and the other is XN+$H_b(R_1)_{3-b}$, or $R_2$ and $R_3$ from a methylene dioxy group
one of $R_4$ and $R_5$ is halogen and the other is halogen substituted 1-6C alkyl, one or both of $R_4$ and $R_5$ are XN+$H_b$ $(R_1)_{3-b}$, or $R_4$ and $R_5$ are joined to form an aromatic or a hetero aromatic ring or a substituted aromatic ring or substituted hetero aromatic ring.

Alternative Embodiment B

The compound of alternative embodiment A having the formula

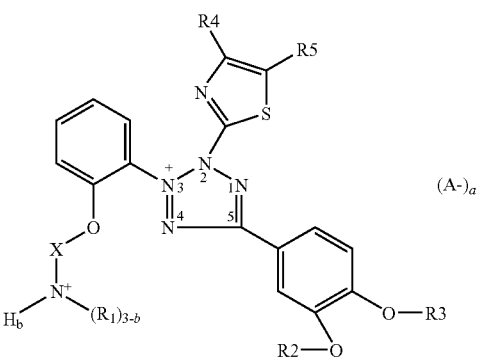

wherein:
A=counter-ion
X=1-6C alkyl
a=1-3
b=0-3
$R_1$=1-3C alkyl
one of $R_2$ and $R_3$ is 1-4C alkyl and the other is XN+$H_b(R_1)_{3-b}$, or $R_2$ and $R_3$ form a methylene dioxy group
$R_4$=CHF$_2$
$R_5$=Halogen.

Alternative Embodiment C

The compound of alternative embodiment B wherein
X is propyl
b is zero
$R_1$ is methyl
$R_2$ and $R_3$ form a methylene dioxy group
$R_4$ is CHF$_2$
$R_5$ is Cl.

Alternative Embodiment D

The compound of alternative embodiment B wherein
X is propyl
b is 1
$R_1$ is methyl
$R_2$ and $R_3$ form a methylene dioxy group
$R_4$ is CHF$_2$
$R_5$ is Cl.

Alternative Embodiment E

The compound of alternative embodiment B wherein
X is propyl
b is zero
$R_1$ is methyl
$R_2$ is trimethylammonium propyl
$R_3$ is methoxy
$R_4$ is CHF$_2$
$R_5$ is Cl.

Alternative Embodiment F

The compound of alternative embodiment A having the formula

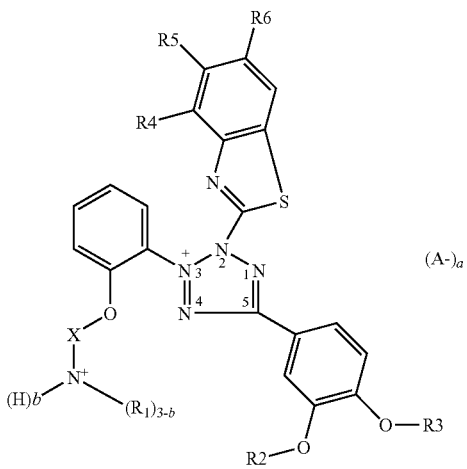

wherein:
a=1-3
A=counter-ion
X=1-6C alkyl
b=0-3
$R_1$=1-3C alkyl
one of $R_2$ and $R_3$ is alkyl and the other is $XN+H_b(R_1)_{3-b}$, or
 $R_2$ and $R_3$ form a methylene dioxy group
one of $R_4$ and $R_5$ is halogen and the other is a halogen substituted 1-6C alkyl, or $R_4$ and $R_5$ are hydrogen
$R_6$=1-4C alkoxy, hydrogen, or halogen.

Alternative Embodiment G

The compound of alternative embodiment F wherein
X is propyl
b is zero
$R_1$ is methyl
$R_2$ is trimethylammonium propyl
$R_3$ is methoxy
$R_4$, $R_5$, and $R_6$ are hydrogen.

Alternative Embodiment H

The compound of alternative embodiment F wherein
X is propyl
$R_1$ is methyl
b is zero
$R_2$ is trimethylammonium propyl
$R_3$ is methyl
$R_4$ and $R_5$ form an aromatic ring
$R_6$ is methoxy.

Alternative Embodiment I

The compound of alternative embodiment F wherein
X is propyl
b is zero
$R_1$ is methyl
$R_2$ is trimethylammonium propyl
$R_3$ is methyl
$R_4$ and $R_5$ are hydrogen
$R_6$ is ethoxy.

Alternative Embodiment J

The compound of alternative embodiment F wherein
X is propyl
b is zero
$R_1$ is methyl
$R_2$ is trimethylammonium propyl
$R_3$ is methyl
$R_4$ and $R_5$ are hydrogen
$R_6$ is bromine.

Alternative Embodiment K

The compound of alternative embodiment A wherein said at least one counter-ion is nitrite, phosphate, hydrogenphosphate, dihydrogen phosphate, hydrogen sulfate, sulfate, hydrogen carbonate, carbonate, methane sulfonate, fluoroborate, bromide, chloride, iodide, or combinations thereof.

Alternative Process L

A method of measuring an analyte contained in a biological fluid, the analyte adapted to produce a proportional color change upon a reaction, the method comprising the acts of:
providing a tetrazolium salt as an indicator, said tetrazolium salt having the formula of

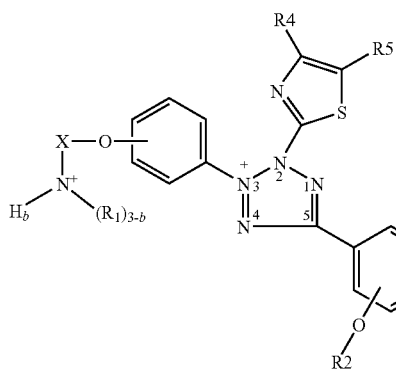

wherein:
A=counter-ion
a=1-3
b=0-3
X=1-6C alkyl or heteroalkyl
$R_1$=1-6C alkyl
one of $R_2$ and $R_3$ is alkyl and the other is $XN+H_b(R_1)_{3-b}$, or
 $R_2$ and $R_3$ form a methylene dioxy group
one of $R_4$ and $R_5$ is halogen and the other is a halogen substituted 1-6C alkyl, one or both of $R_4$ and $R_5$ are $XN+H_b(R_1)_{3-b}$, or $R_4$ and $R_5$ are joined to form an aromatic or a hetero aromatic ring or a substituted aromatic ring or substituted hetero aromatic ring; and
determining the concentration of said analyte in said biological fluid with the assistance of said tetrazolium salt as the indicator.

Alternative Process M

The method of alternative process L wherein said analyte is glucose.

Alternative Process N

The method of alternative process M wherein said biological fluid is whole blood.

Alternative Process O

The method of alternative process M wherein said tetrazolium salt has the formula

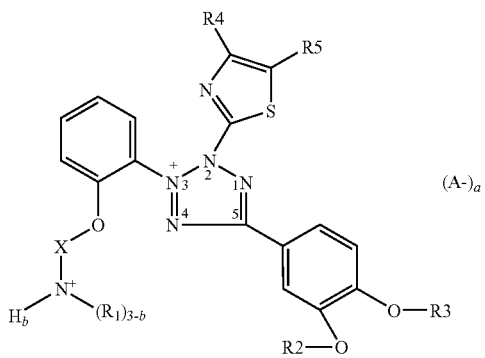

wherein:
A=counter-ion
X=1-6C alkyl
a=1-3
b=0-3
$R_1$=1-3C alkyl
one of $R_2$ and $R_3$ is 1-4C alkyl and the other is $XN+H_b(R_1)_{3-b}$, or $R_2$ and $R_3$ form a methylene dioxy group
$R_4$=$CHF_2$
$R_5$=Halogen.

Alternative Process P

The method of alternative process O wherein
X is propyl
b is zero
$R_1$ is methyl
$R_2$ and $R_3$ form a methylene dioxy group
$R_4$ is $CHF_2$
$R_5$ is Cl.

Alternative Process Q

The method of alternative process O wherein
X is propyl
b is 1
$R_1$ is methyl
$R_2$ and $R_3$ form a methylene dioxy group
$R_4$ is $CHF_2$
$R_5$ is Cl.

Alternative Process R

A method of alternative process O wherein
X is propyl
b is zero
$R_1$ is methyl
$R_2$ is trimethylammonium propyl
$R_3$ is methoxy
$R_4$ is $CHF_2$
$R_5$ is Cl

Alternative Process S

The method of alternative process L having the formula

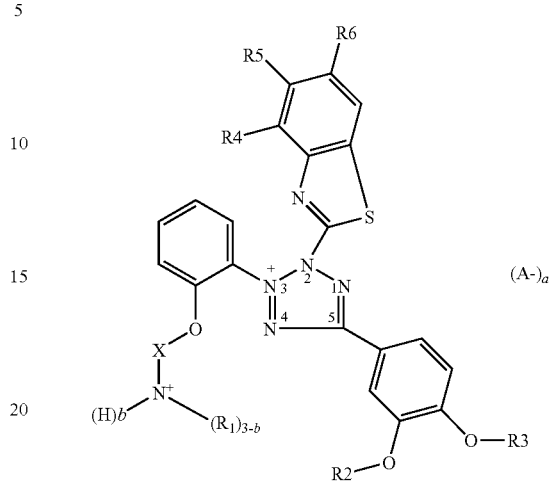

wherein:
a=1-3
A=counter-ion
X=1-6C alkyl
b=0-3
$R_1$=1-3C alkyl
one of $R_2$ and $R_3$ is alkyl and the other is $XN+H_b(R_1)_{3-b}$, or $R_2$ and $R_3$ form a methylene dioxy group
one of $R_4$ and $R_5$ is halogen and the other is a halogen substituted 1-6C alkyl, or $R_4$ and $R_5$ are hydrogen
$R_6$=1-4C alkoxy, hydrogen, or halogen.

Alternative Process T

The method of alternative process S wherein
X is propyl
b is zero
$R_1$ is methyl
$R_2$ is trimethylammonium propyl
$R_3$ is methoxy
$R_4$, $R_5$, and $R_6$ are hydrogen.

Alternative Process U

A method of alternative process S wherein
X is propyl
$R_1$ is methyl
b is zero
$R_2$ is trimethylammonium propyl
$R_3$ is methyl
$R_4$ and $R_5$ form an aromatic ring
$R_6$ is methoxy.

Alternative Process V

The method of alternative process S wherein
X is propyl
b is zero
$R_1$ is methyl
$R_2$ is trimethylammonium propyl
$R_3$ is methyl
$R_4$ and $R_5$ are hydrogen
$R_6$ is ethoxy.

Alternative Process W

The method of alternative process S wherein
X is propyl
b is zero
R$_1$ is methyl
R$_2$ is trimethylammonium propyl
R$_3$ is methyl
R$_4$ and R$_5$ are hydrogen
R$_6$ is bromine.

Alternative Process X

The method of alternative process L wherein said at least one counter-ion is nitrite, phosphate, hydrogenphosphate, dihydrogen phosphate, hydrogen sulfate, sulfate, hydrogen carbonate, carbonate, methane sulfonate, fluoroborate, bromide, chloride, iodide, or combinations thereof.

Alternative Process Y

A method of increasing the solubility of thiazoyl tetrazolium salts having the thiazoyl group attached at the third nitrogen atom of the tetrazolium ring, the method comprising adding at least one trialkyl ammonium alkoxy group as a substituent to the thiazoyl tetrazolium salt.

Alternative Process Z

The method of alternative process Y wherein said thiazoyl tetrazolium salt has phenyl substituents at the third nitrogen atom and at the carbon atom of the tetrazolium ring.

Alternative Process AA

The method of alternative process Z wherein said at least one trialkyl ammonium alkoxy group is a trimethyl ammonium propoxy group.

Alternative Process BB

The method of alternative process Z wherein said at least one trialkyl ammonium alkoxy group is a substituent of said phenyl groups.

Alternative Process CC

The method of alternative process Z wherein at least one trialkyl ammonium alkoxy group is a substituent of both of said phenyl substituents.

Alternative Process DD

The method of alternative process Z wherein said thiazoyl group is a benzo thiazoyl group.

Alternative Process EE

The method of alternative process Z wherein said thiazoyl tetrazolium salt has counterions of nitrite, phosphate, hydrogen phosphate, dihydrogen phosphate, hydrogen sulfate, sulfate, hydrogen carbonate, carbonate, methane sulfonate, fluoroborate, bromode, chloride, iodide, or combinations thereof.

Alternative Process FF

The method of alternative process EE wherein said counterions are bromo nitrite, dibromo nitrite, or tribromide.

The invention claimed is:
1. A compound having the formula

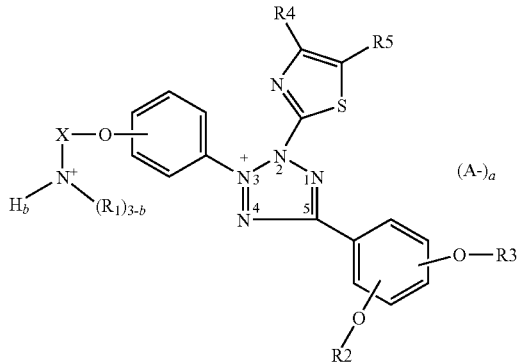

wherein:
A = counter-ion
a = 1-3
b = 0-3
X = 1-6C alkyl or heteroalkyl
R$_1$ = 1-6C alkyl
one of R$_2$ and R$_3$ is alkyl and the other is XN+H$_b$(R$_1$)$_{3-b}$, or R$_2$ and R$_3$ form a methylene dioxy group
one of R$_4$ and R$_5$ is halogen and the other is halogen substituted 1-6C alkyl, both of R$_4$ and R$_5$ being XN+H$_b$(R$_1$)$_{3-b}$, or R$_4$ and R$_5$ are joined to form an aromatic ring or a substituted aromatic ring.

2. The compound of claim 1 having the formula

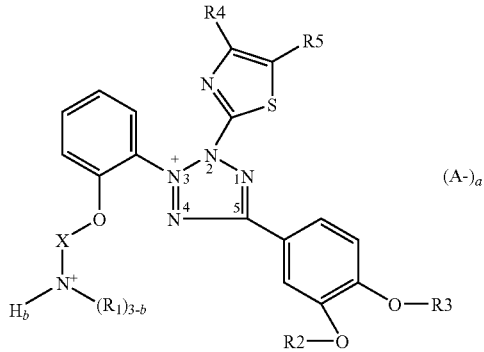

wherein:
A = counter-ion
X = 1-6C alkyl
a = 1-3
b = 0-3
R$_1$ = 1-3C alkyl
one of R$_2$ and R$_3$ is 1-4C alkyl and the other is XN+H$_b$(R$_1$)$_{3-b}$, or R$_2$ and R$_3$ form a methylene dioxy group
R$_4$ = CHF$_2$
R$_5$ = Halogen.

3. The compound of claim 2, wherein
X is propyl
b is zero
R$_1$ is methyl
R$_2$ and R$_3$ form a methylene dioxy group
R$_4$ is CHF$_2$
R$_5$ is Cl.

4. The compound of claim 2, wherein
X is propyl
b is 1
$R_1$ is methyl
$R_2$ and $R_3$ form a methylene dioxy group
$R_4$ is $CHF_2$
$R_5$ is Cl.

5. The compound of claim 2, wherein
X is propyl
b is zero
$R_1$ is methyl
$R_2$ is trimethylammonium propyl
$R_3$ is methyl;
$R_4$ is $CHF_2$
$R_5$ is Cl.

6. The compound of claim 1 having the formula

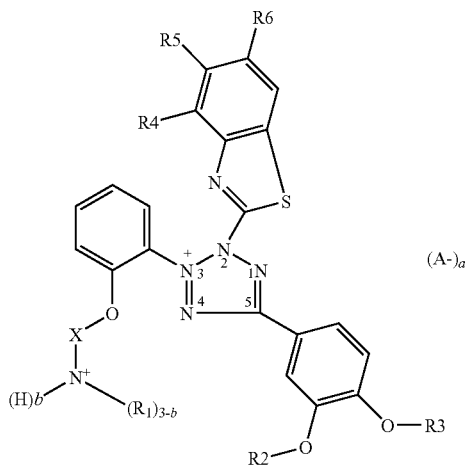

wherein:
a = 1-3
A = counter-ion
X = 1-6C alkyl
b = 0-3
$R_1$ = 1-3C alkyl
one of $R_2$ and $R_3$ is alkyl and the other is $XN+H_b(R_1)_{3-b}$, or $R_2$ and $R_3$ form a methylene dioxy group
one of $R_4$ and $R_5$ is halogen and the other is a halogen substituted 1-6C alkyl, or $R_4$ and $R_5$ are hydrogen
$R_6$ = 1-4C alkoxy, hydrogen, or halogen.

7. The compound of claim 6, wherein
X is propyl
b is zero
$R_1$ is methyl
$R_2$ is trimethylammonium propyl
$R_3$ is methyl
$R_4$, $R_5$, and $R_6$ are hydrogen.

8. The compound of claim 6, wherein
X is propyl
$R_1$ is methyl
b is zero
$R_2$ is trimethylammonium propyl
$R_3$ is methyl
$R_4$ and $R_5$ form an aromatic ring
$R_6$ is methoxy.

9. The compound of claim 6, wherein
X is propyl
b is zero
$R_1$ is methyl
$R_2$ is trimethylammonium propyl
$R_3$ is methyl
$R_4$ and $R_5$ are hydrogen
$R_6$ is ethoxy.

10. The compound of claim 6, wherein
X is propyl
b is zero
$R_1$ is methyl
$R_2$ is trimethylammonium propyl
$R_3$ is methyl
$R_4$ and $R_5$ are hydrogen
$R_6$ is bromine.

11. The compound of claim 1, wherein said at least one counter-ion is nitrite, phosphate, hydrogenphosphate, dihydrogen phosphate, hydrogen sulfate, sulfate, hydrogen carbonate, carbonate, methane sulfonate, fluoroborate, bromide, chloride, iodide, or combinations thereof.

12. The compound of claim 1, wherein one of $R_4$ and $R_5$ is halogen and the other is a halogen substituted 1-6C alkyl.

13. The compound of claim 1, wherein $R_4$ and $R_5$ are joined to form an aromatic ring.

14. The compound of claim 13, wherein $R_4$ and $R_5$ are joined to form a 6-membered aromatic ring.

* * * * *